US006539251B2

(12) United States Patent
Beck et al.

(10) Patent No.: US 6,539,251 B2
(45) Date of Patent: Mar. 25, 2003

(54) OCULAR IONTOPHORETIC APPARATUS

(75) Inventors: Jon E. Beck, Salt Lake City, UT (US); Alex Koss, Salt Lake City, UT (US)

(73) Assignee: Iomed, Inc., Salt Lake City, UT (US)

( * ) Notice: Subject to any disclaimer, the term of this patent is extended or adjusted under 35 U.S.C. 154(b) by 0 days.

(21) Appl. No.: 09/922,558

(22) Filed: Aug. 3, 2001

(65) Prior Publication Data

US 2002/0016575 A1 Feb. 7, 2002

Related U.S. Application Data

(63) Continuation-in-part of application No. 09/318,181, filed on May 25, 1999, now Pat. No. 6,319,240, and a continuation-in-part of application No. 09/599,245, filed on Jun. 22, 2000
(60) Provisional application No. 60/184,498, filed on Feb. 23, 2000.

(51) Int. Cl.[7] .............................................. A61B 17/20
(52) U.S. Cl. ..................... 604/20; 604/294; 607/149
(58) Field of Search .......................... 604/521, 20, 294, 604/300–302, 176, 295; 607/149

(56) References Cited

U.S. PATENT DOCUMENTS

| | | | |
|---|---|---|---|
| 542,508 A | 7/1895 | Van Tuyl, Jr. | |
| 2,525,381 A | 10/1950 | Tower | 128/172.1 |
| 3,122,137 A | 2/1964 | Erlanger | 128/172.1 |
| 3,392,725 A | * 7/1968 | Behney | |
| 4,416,274 A | 11/1983 | Jacobsen et al. | 604/20 |
| 4,564,016 A | * 1/1986 | Maurice et al. | |
| 4,708,716 A | 11/1987 | Sibalis | 604/20 |
| 4,955,378 A | 9/1990 | Grasso | 128/421 |
| 5,053,000 A | 10/1991 | Booth et al. | 604/20 |
| 5,160,316 A | 11/1992 | Henley | 604/20 |
| 5,169,384 A | 12/1992 | Bosniak et al. | 604/20 |
| 5,174,304 A | 12/1992 | Latina et al. | 128/793 |
| 5,833,701 A | * 11/1998 | Gordon | |
| 6,101,411 A | 8/2000 | Newsome | 604/20 |
| 6,154,671 A | 11/2000 | Parel et al. | 604/20 |

FOREIGN PATENT DOCUMENTS

| | | |
|---|---|---|
| FR | 98-00009 | 1/1998 |
| GB | 2 177 928 A | 2/1987 |
| SU | 939 019 | 6/1982 |
| WO | WO 99/40967 | 8/1999 |

OTHER PUBLICATIONS

Publication entitled "Investigative Ophthalmology & Visual Science," vol. 31, No. 5, May 1990, pp 909–916, "Article on Regional Ocular Gentamicin Levels after Transcorneal and Transscleral Iontophoresis," by Robyn E. Grossman, Douglas F. Chu, and David A. Lee.
Report entitled "Transscleral Iontophoresis of Gentamicin in Monkeys," by Michael Barza, Cornelia Peckman, and Jules Branum, No. 6, pp 1033–1036.
Publication entitled "Journal of Ocular Pharmacology," vol. 10, No. 1, 1994, pp 69–81, "The Role of Iontophoresis in Ocular Drug Delivery," by David Sarraf and David A. Lee.
Publication entitled "Ocular Coulomb Controlled Iontophoresis," I. Nose, J–M. Parel, W. Lee, F. Cohen, Y. DeKosac, C. Rowaan, A. Paldano, V. Jallet, P. Soderberg, and J. Davis, referenced in Investigative Ophthalmology & Visual Science, Feb. 15, 1996, vol. 37, Nno. 3, p. S41.
Publication entitled "Iontophoresis of Dexamethasone in the Treatment of Endotoxin–Induced–Uveitis in Rats," Francine F. Behar–Cohen, Jean–Marie Parel, Yves Pouliquen, Beatrice Thillaye–Goldenberg, Oliver Goureau, Silke Heydolph, Yves Courtois and Yvonne De Kozak, 1997, pp 533–545.

* cited by examiner

Primary Examiner—Mark Bockelman
(74) Attorney, Agent, or Firm—Factor & Partners

(57) ABSTRACT

An ocular iontophoretic apparatus comprising a reservoir which includes a outer rim. The outer rim includes a barrier. The barrier is positionable upon the surface of the eye and serves to provide a seal between the reservoir and the surface of the eye. In turn the passage of fluid across the barrier into and out of the reservoir is substantially precluded.

12 Claims, 4 Drawing Sheets

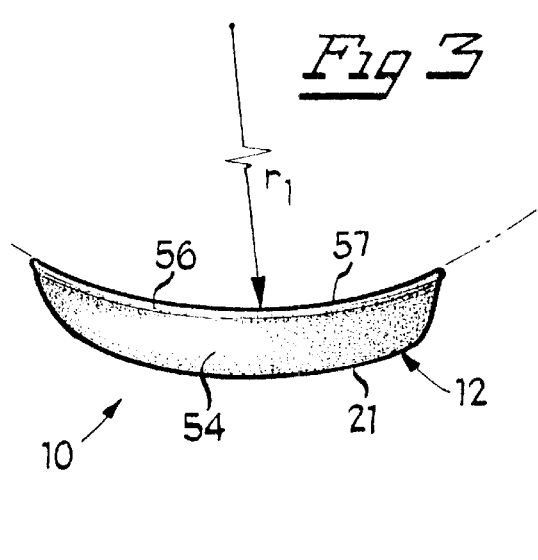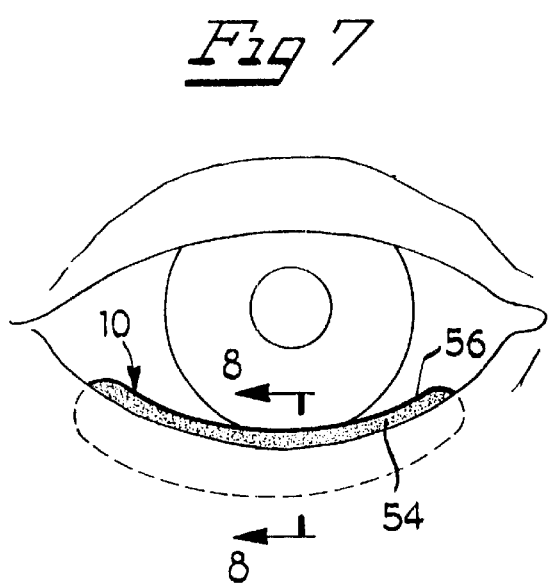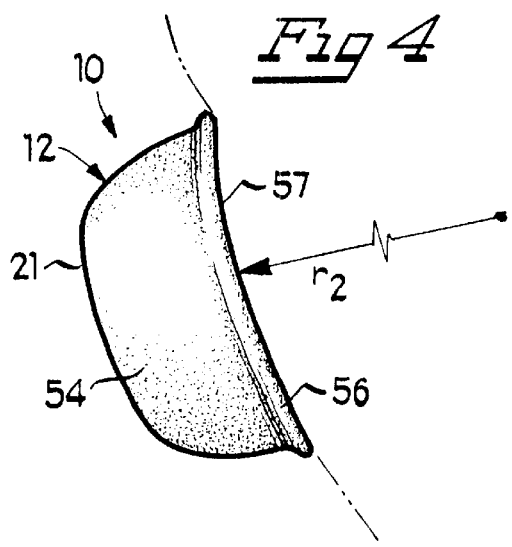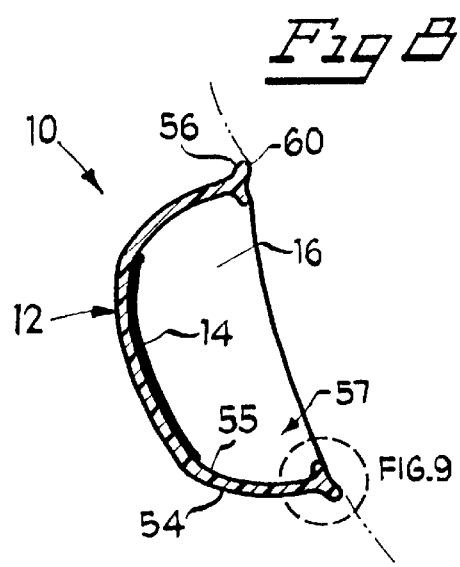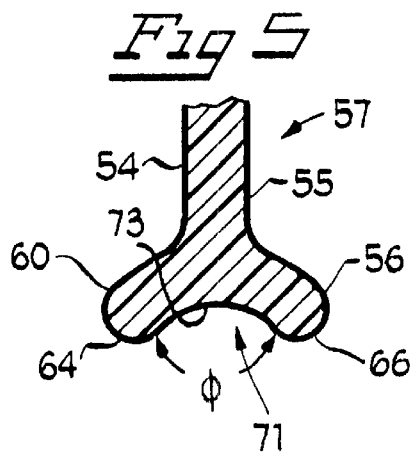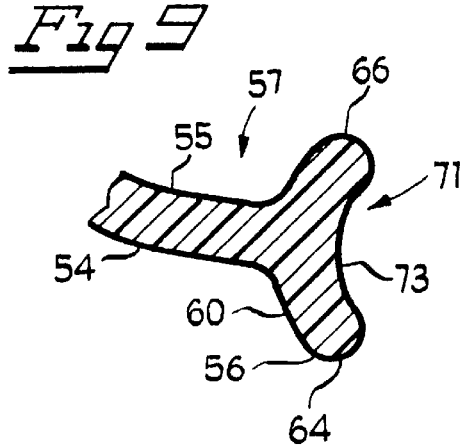

OCULAR IONTOPHORETIC APPARATUS

PRIOR APPLICATIONS

This application is a continuation-in-part of U.S. application Ser. No. 09/318,181 filed May 25, 1999 now U.S. Pat. No. 6,319,240, and, this application is also a continuation-in-part of U.S. application Ser. No. 09/599,245 filed Jun. 22, 2000 pending which claims the priority of U.S. Provisional Application Serial No. 60/184,498 filed Feb. 23, 2000.

BACKGROUND OF THE INVENTION

1. Field of the Invention

The present invention is directed to ocular iontophoretic apparatuses, and more particularly, to an ocular iontophoretic apparatus having an improved seal about the surface of the eye and configured for positioning about the sclera.

2. Background Art

The use of ocular iontophoretic devices has been known in the art. Such devices have been used in an attempt to administer a drug through an electromotive force which drives ionic chemicals into and through the eye tissue so that they can be absorbed at the site or, by adjacent tissues and by blood vessels.

Among other problems, difficulties can be incurred with the placement of these devices onto the surface of the eye of a patient. Certain prior art devices encompass a large portion of the eye and cover or interface with the cornea. Specifically, due to the cumbersome nature of these prior art devices and their limited ability to specifically define the placement, treatment site and sharply defined region of of medicament exposure, such devices greatly obstruct vision and the natural movements of the eye during treatment.

Other solutions provide inadequate sealing of the device on the surface of the eye of the patient. As such, current which is used to drive the medicament through the sclera can instead undesirably be conducted via the saline ionic tear fluid of the eye along the surface of the eye and other undesirable tissues. Further, such inadequate seals permit the ingress of tears into the medicament reservoir itself, and adversely contaminates the specific ionically charged drug solution with sodium and chloride ions.

Accordingly, it is an object of the invention to provide an ocular iontophoretic apparatus which provides improved comfort for the user.

It is likewise an object of the invention to provide an improved barrier to seal and preclude the passage of fluid thereacross.

It is another object of the invention to minimize the electrical current from inadvertent and excess shunting via surrounding tear film interference.

These and other objects of the invention will become apparent in light of the specification and claims appended hereto.

SUMMARY OF THE INVENTION

The invention comprises an ocular iontophoretic apparatus. The ocular iontophoretic apparatus includes a reservoir having an outer rim. The outer rim includes a barrier which is positionable upon the surface of the eye. The barrier provides a seal between the reservoir and the surface of the eye, to, in turn, substantially preclude the passage of fluid into and out of the barrier.

In a preferred embodiment, the barrier includes means for forming a vacuum/suction seal with a surface of the eye. In one such embodiment, the barrier comprises a first lobe and a second lobe. The two lobes extend away from each other at a predetermined angle. In another such preferred embodiment, the barrier comprises a contact region having a concave configuration.

In a preferred embodiment, a portion of the barrier comprises a material having a Shore A hardness ranging between 5 and 60, and preferably between 5 and 25 to, in turn, provide a substantially fluid tight seal between the barrier and the surface of the eye.

In another preferred embodiment, the barrier includes a first region and a second region. The second region comprises a material having a greater hardness than that of the first region. In one such preferred embodiment, the second region comprises a hardness which may be up to 90 Shore A as well as extend beyond that of Shore A scale 15.

In yet another preferred embodiment, the cross-sectional configuration of the barrier comprises one of the group consisting of: circular, squared, oval, elliptical, asymmetrical and arcuate.

In a preferred embodiment, the outer rim is configured so as to follow the contours of a particular region of the sciera of an eye, to in turn, facilitate the uniform contact of the barrier against the surface thereof. In one such embodiment, the outer rim includes at least a double arcuate configuration, to, in turn, facilitate the uniform contact of the barrier against the surface of an eye. Preferably, the first arcuate configuration includes a radius of curvature which ranges between 10 and 14 mm, and the second arcuate configuration includes a radius of curvature which ranges between 10 and 14 mm.

In a preferred embodiment, the apparatus further comprises a first means for vacuum sealing the reservoir against the surface of an eye of a patient. In one embodiment, the first vacuum sealing means comprises the cooperation of the barrier member and the seal member to facilitate the egress of a quantity of material from within the reservoir, while substantially precluding the ingress of material into the reservoir. In another embodiment, the first vacuum sealing means further includes a valve capable of selectively placing the reservoir in fluid communication with ambient surrounding conditions.

The invention likewise comprises an ocular iontophoretic apparatus which comprises a reservoir having an outer shell. The outer shell includes a transverse radius of curvature to facilitate placement of the apparatus on the sclera of an eye, while substantially precluding contact thereof with the cornea of an eye.

In one preferred embodiment, the transverse radius of curvature which is at least 6 mm.

In another preferred embodiment, the apparatus includes an outer rim. The outer rim includes at least a double arcuate configuration. Such a configuration facilitates the uniform contact of the barrier against the surface of an eye. In one such embodiment, the first arcuate configuration includes a radius of curvature which ranges between 10 and 14 mm, and the second arcuate configuration includes a radius of curvature which ranges between 10 and 14 mm.

The invention likewise comprises a method of sealing an ocular iontophoretic apparatus against the surface of an eye. The method comprises the step of providing an ocular iontophoretic apparatus having an outer rim which includes a barrier having a concave contact region. Once provided, the barrier is positioned so as to engage the concave contact region with the surface of the eye. Next, at least a portion of the air trapped between the concave contact region and the surface of the eye is evacuated which creates a vacuum seal between the surface of the eye and the concave contact region of the barrier.

In one embodiment, the step of positioning the barrier comprises the step of positioning the barrier below the cornea of the eye.

In another embodiment, the method further comprises the step of positioning the eyelid of the patient over at least a portion of the ocular iontophoretic apparatus below the eyelid of the patient.

The invention likewise comprises a method of sealing an ocular iontophoretic apparatus against the surface of an eye. The method comprises the steps of providing an ocular iontophoretic apparatus having a reservoir, an outer rim which includes a barrier, positioning the barrier upon the surface of the eye, evacuating at least a portion of a material from within the reservoir, and, creating a vacuum seal between the surface of the eye and the reservoir.

BRIEF DESCRIPTION OF THE DRAWINGS

FIG. 3 of the drawings is a top plan view of the apparatus shown in FIG. 1;

FIG. 4 of the drawings is a side elevational view of the apparatus shown in FIG. 1;

FIG. 5 of the drawings is a partial cross-sectional view of the apparatus shown in FIG. 1 taken generally about lines 5—5 of FIG. 2;

FIG. 7 of the drawings is a top plan view of the embodiment of the apparatus shown in FIG. 1, showing, in particular, the apparatus in operation in an ocular environment;

FIG. 8 of the drawings is a partial cross-sectional view of the apparatus taken generally about lines 8—8 of FIG. 7;

FIG. 9 of the drawings is a partial cross-sectional view of the apparatus taken generally about lines 9—9 of FIG. 8;

BEST MODE FOR PRACTICING THE INVENTION

Figure 1:
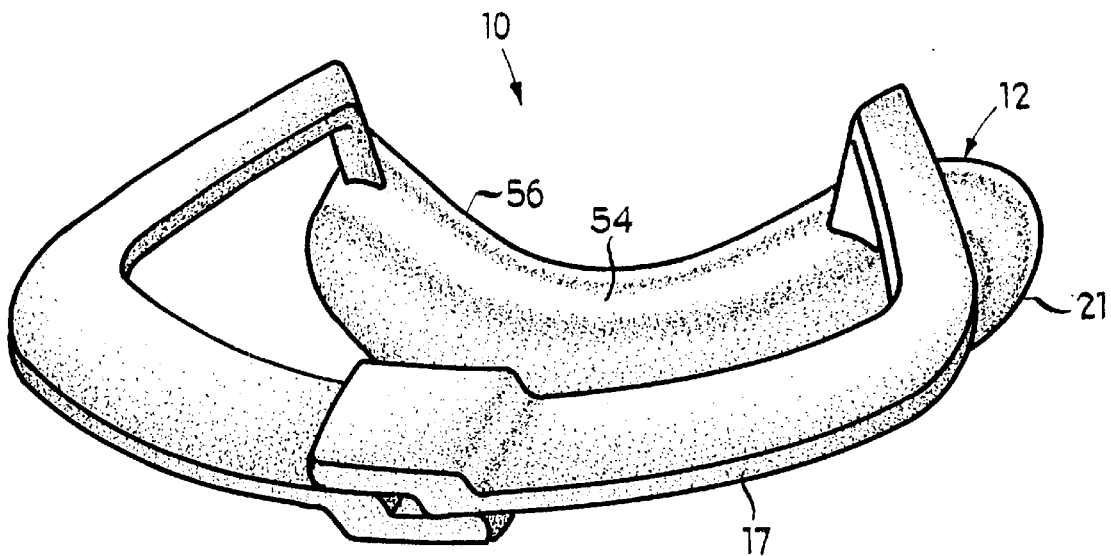
FIG. 1 of the drawings is a front perspective view of one embodiment of the apparatus of the present invention.

While this invention is susceptible of embodiment in many different forms, there is shown in the drawings and will be described in detail, several specific embodiments with the understanding that the present disclosure is to be considered as an exemplification of the principles of the invention and is not intended to limit the invention to the embodiments illustrated.

Figure 2:
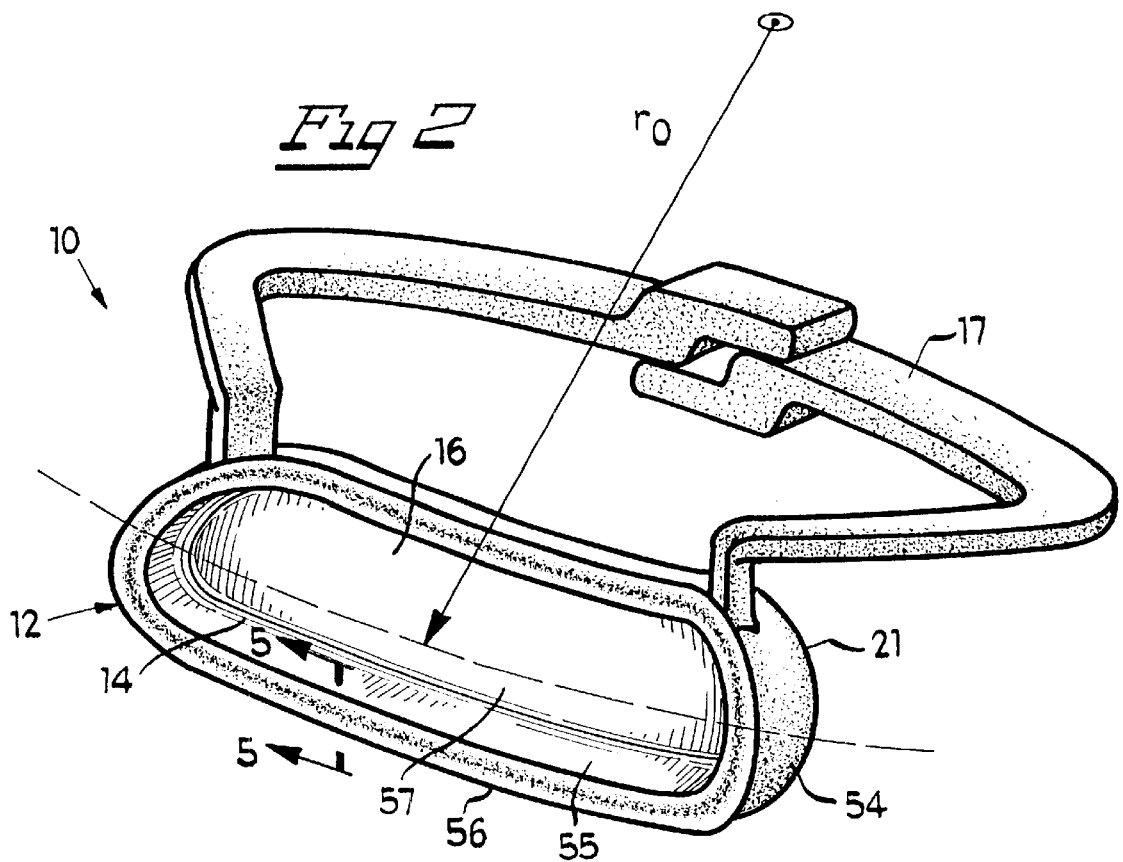
FIG. 2 of the drawings is a back perspective view of the embodiment of the apparatus of the present invention shown in FIG. 1.

Referring now to the Figures, and, in particular, FIGS. 1 and 2, one embodiment of ocular iontophoretic apparatus is shown generally at 10. As shown in FIG. 2, ocular iontophoretic apparatus 10 comprises reservoir 12, electrode 14, medicament containment member 16 and handle 17. Handle 17 is explained in detail in co-pending application Ser. No. 09/599,245 entitled "Ocular iontophoretic Apparatus Handle," and, as such, will not be discussed in detail herein. As will be understood, the ocular iontophoretic apparatus is operatively associated with the surface of the eye of a patient for the application of medicament to the eye, to, for example, combat eye infections. Specifically, medicament from the medicament containment member is driven by an electric current which results from the applying of a potential across two electrodes, namely electrode 14, and another electrode which may be separate and applicable to another portion of a patient (such as the back of the neck).

The medicament that is retained in reservoir 12 may comprise various medicaments and/or medicament carriers in a variety of forms, for example, but not limited to, in aqueous form, in a hydrogel form, or in the form of a hydrated solid, such as, for example, a polymer matrix. Indeed, the apparatus is not limited to use in association with any particular medicament or particular form of medicament carrier.

Referring now to FIG. 2, reservoir 12 comprises shell member 21 which includes outside surface 54, inside surface 55, and outer rim 56. Inside surface 55 is formed in such a way as to define cavity 57. As shown in FIG. 2, electrode 14 and medicament containment member 16 are positioned within cavity 57.

Figure 10:
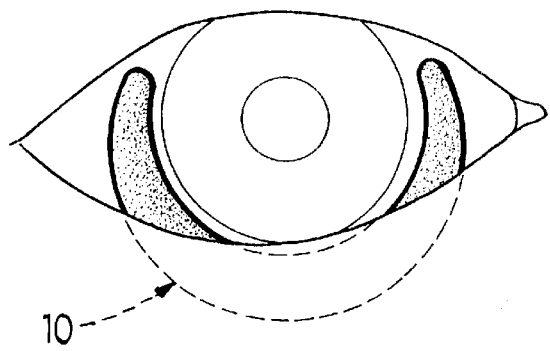
FIG. 10 of the drawings is a front view of another embodiment of the apparatus.
Figure 11:
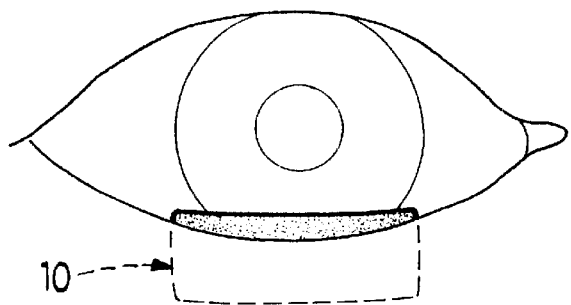
FIG. 11 of the drawings is a front view of another embodiment of the apparatus.
Figure 12:
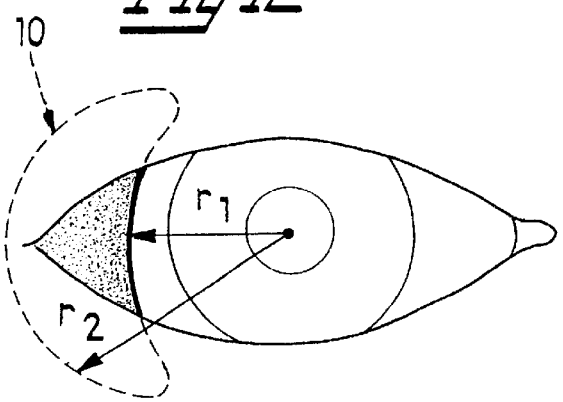
FIG. 12 of the drawings is a front view of another embodiment of the apparatus.

Shell member 21 is likewise shown in FIG. 2 as comprising a configuration which facilitates the placement thereof along the sclera below the cornea. Shell member 21 generally comprises a kidney shaped member which generally follows the contours of the lower region of the cornea. Of course, other shapes of the shell member are likewise contemplated. For example, the shell member may comprise a rectangular configuration (FIG. 11), a modified triangular shape (FIG. 12), an extended kidney which may extend any distance around the eye of the patient (FIG. 10) or another shape or configuration. While not specifically limited thereto, the shape is related to the particular positioning of the shell member. With respect to the member shown in FIG. 1, shell member includes a transverse radius of curvature $r_0$ which is at least about 6 mm. Indeed, the width of the shell member, as well as the length and the radius of curvature can be varied as long as the placement can be made proximate to the cornea and/or limbus and specific structures such as the cornea itself can be avoided. For example, the radius of curvature of the embodiment shown in FIG. 11 is infinite as the surfaces are substantially planar. Generally, shell member 21 comprises a plastic or silicone member having a Shore A hardness ranging between 15 and 90. Also, other materials which are rigid (i.e., polycarbonates, polyesters, etc.) are likewise contemplated. As such, the shell member has a certain amount of flexibility while nevertheless maintaining its integrity so as to facilitate the retention of medicament and the medicament containment member within the reservoir.

Figure 14:
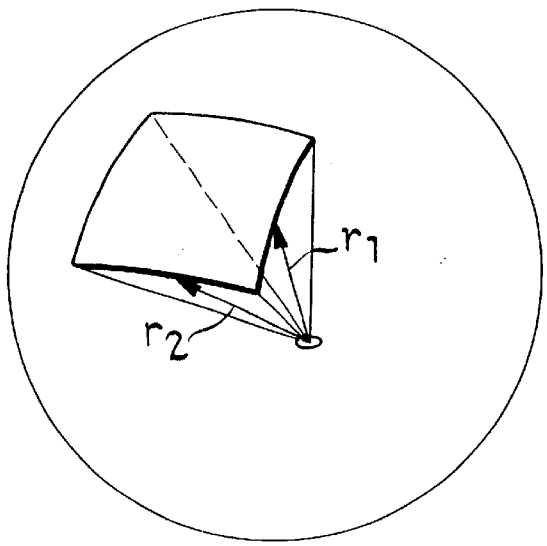
FIG. 14 of the drawings is a schematic view of an eye of a patient showing in particular angles $r_0$ and $r_1$.

Referring now to FIGS. 3 and 4, rim 56 is likewise configured so as to facilitate the positioning of the apparatus along the sclera below, along side or above the cornea. As such, rim 56 generally includes a double arcuate configuration, namely an arcuate configuration $r_1$ (FIG. 3) extending longitudinally from end to end of the apparatus and arcuate configuration $r_2$ (FIG. 4) extending transversely from top to bottom of the apparatus. The first arcuate configuration $r_1$ has an radius of curvature that ranges between about 10 and 14 mm and most preferably about 12 mm, and second arcuate configuration $r_2$ includes that ranges between about 10 and 14 mm and most preferably about 12 mm. In certain embodiments, rim 56 may include additional radii of curvature depending on the positioning and application of the apparatus. Additionally, the radii of curvature can be varied depending on the size of the eyeball of the patient and the positioning and placement of the shell member relative to the eye (i.e. as shown in FIG. 14, the two radii are related to the spherical curvature of the eye at any given position of the apparatus).

Figure 13:
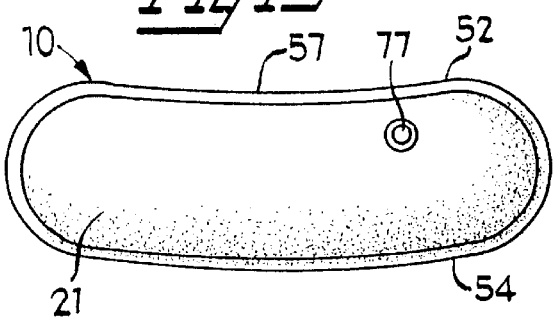
FIG. 13 of the drawings is a front view of a apparatus of the invention showing in particular a valve.

In certain embodiments of the invention, and as shown in FIG. 13, shell member 21 may include first means for vacuum sealing cavity 57 against the surface of the eye. For example, shell member 21 may include valve 77 positioned on shell member 21 extending from inner surface 52 to outer surface 54. The valve permits the egress of material (i.e. air or fluid/air) from within the cavity as the cavity is pressed against the surface of the eye. Once the material is removed, and the cavity returns toward its original configuration, a vacuum/suction effect is achieved between cavity 57 and the surface of the eye. In other embodiments, the vacuum sealing means may comprise the cooperation of the shell member with a barrier (such as the barrier shown in FIG. 6f). In such an embodiments, as the shell member is depressed against the eye, the barrier is configured so as to permit the egress of material.

Referring now to FIG. 5, outer rim 56 further includes barrier 60 which extends about the outer rim. Barrier 60 is configured so as to preclude the ingress of tear fluid as well as other fluids into reservoir 12. Moreover, barrier 60 likewise precludes the egress of medicament from within reservoir 12. In the embodiment shown in FIG. 5 in detail, barrier 60 includes lobes 64 and 66 which extend outwardly from shell 21. The lobes are angularly displaced relative to each other at an angle ϕ ranging between just greater than 0 and just less than 180 degrees. Moreover, each lobe includes contact region 73 which is the region of the respective lobe that, at least in partially, contacts the surface of the eye. Lobes 64 and 66 generally comprise a silicone and/or other flexible material having a Shore A hardness ranging between 5 and 60, and most preferably 5 to 25. Indeed, in certain embodiments, the material may be soft so as to have a gel-like appearance and have certain adhesion properties (i.e. lightly cross-linked silicone).

Together, lobes 64 and 66 form a second means for vacuum/suction sealing the barrier with the surface of the eye. Indeed, and as will be explained below relative to operation thereof, lobes 64 and 66 are pressed against the surface of the eye during positioning, wherein a vacuum/ suction seal is formed with the surface of the eye. This seal effectively renders the barrier impervious. In addition, the lobes provide a double seal surface; in the event that one of the lobes inadvertently detaches from the surface of the eye, the second lobe can maintain the seal against the surface of the eye. In certain embodiments, barrier 60 and shell member 21 may comprise an identical material.

Figure 6A:
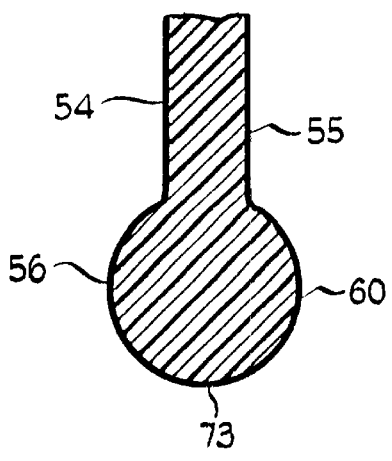
FIG. 6a of the drawings is a partial cross-sectional view showing in particular an alternate embodiment of the barrier.
Figure 6D:
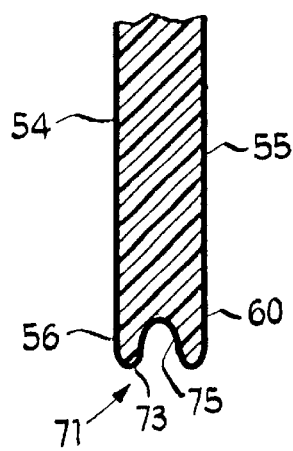
FIG. 6d of the drawings is a partial cross-sectional view showing in particular a fifth embodiment of the barrier.
Figure 6B:
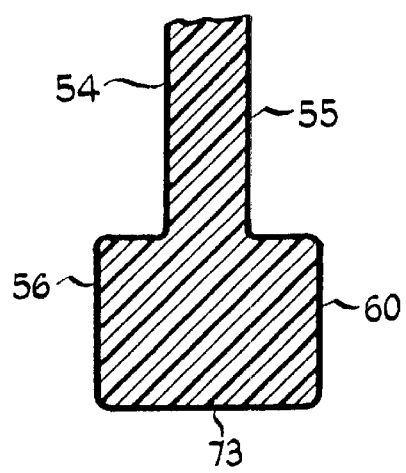
FIG. 6b of the drawings is a partial cross-sectional view showing in particular a third embodiment of the barrier.
Figure 6E:
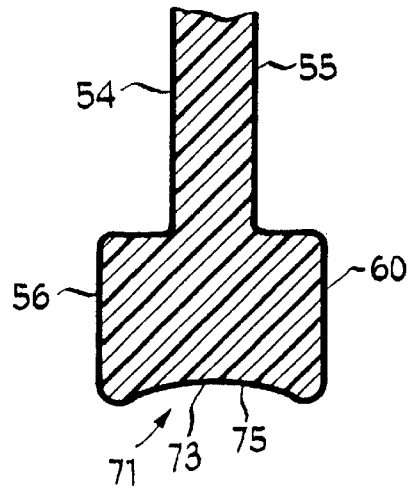
FIG. 6e of the drawings is a partial cross-sectional view showing in particular a sixth embodiment of the barrier.

In other embodiments, barrier 60 may comprise a different geometric configuration. For example, barrier 60 may comprise a circular (FIG. 6a), rectangular (FIGS. 6b and 6e), elliptical, oval, arcuate (FIG. 6d) cross section, among others. As can be seen in these figures, certain embodiments include vacuum/suction forming means 71 which contacts and interfaces with the surface of the eye, whereas other embodiments rely on the hardness of the barrier material and the tactile nature thereof. In particular, vacuum/suction forming means 71 may comprise various shapes having contact region 73 shaped into a concave structure, such as concave structure 75 of the embodiments shown in FIGS. 6d and 6e.

In another embodiment, as explained above, and, as shown in FIG. 6f, the barrier may be configured so as to include an asymmetrical member which extends outwardly. Such a configuration is particularly useful in the embodiment described above wherein the barrier cooperates with the shell member so as to form a first means for vacuum sealing. Indeed, such a seal configuration permits the egress of material from within the cavity member when the shell member is compressed against the eye, yet, precludes the ingress of material into the cavity when the shell member is released.

Figure 6C:
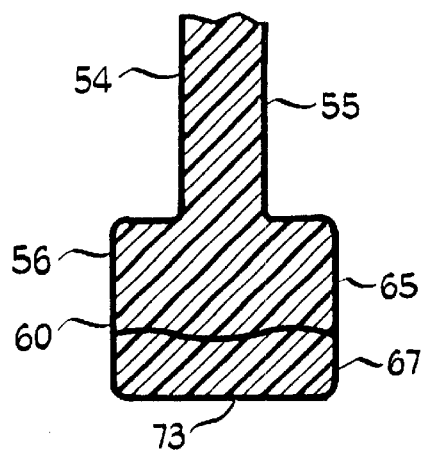
FIG. 6c of the drawings is a partial cross-sectional view showing in particular a fourth embodiment of the barrier.

Moreover, in certain of these embodiments, the hardness of barrier 60 may vary within the barrier itself. For example, barrier 60 may comprise a material having a lower hardness than the shell member, i.e. the shell may be more rigid (a Shore A hardness of about 5 to 90 as well as more rigid materials identified above) whereas the barrier may be less rigid (a Shore A hardness of about 5 to 60, and more preferably 5 to 25). One such embodiment is shown in FIG. 6c, namely, upper region 65 may have a hardness which is greater than that of region 67 therebelow. Barriers of differing hardness can likewise be employed with the barriers configuration shown in FIGS. 5–8.

In operation, the apparatus is provided to a doctor or other medical professional, for example. In certain embodiments, the medical professional applies the medicament to medicament containment member. In other embodiments, the medicament is placed within the medicament containment member during manufacture. In either case, once the medicament is placed within the medicament containment member, the device is ready for use.

Next, the medical professional places the apparatus upon the surface of the eye that is to be treated. In particular, as shown in FIGS. 7 and 8, the apparatus is placed such that the apparatus extends along the sclera of the eye any one of below, to the side or above the cornea so that barrier 60 contacts the surface of the eye. As shown in FIG. 9, as the barrier contacts the surface of the eye, lobes 64 and 66 spread such that region 73 at least partially abuts the surface and evacuates a portion of the air which is trapped between region 73 and the surface of the eye. In turn, region 73 and the surface of the eye cooperate to form a vacuum/suction seal against the surface of the eye. Other embodiments, such as embodiments shown in FIGS. 6d and 6e likewise form a vacuum/suction seal against the surface of the eye, whereas the embodiments shown in FIGS. 6a through 6c rely on the hardness of the material itself and its tactile nature to adequately seal against the surface of the eye.

Figure 6F:
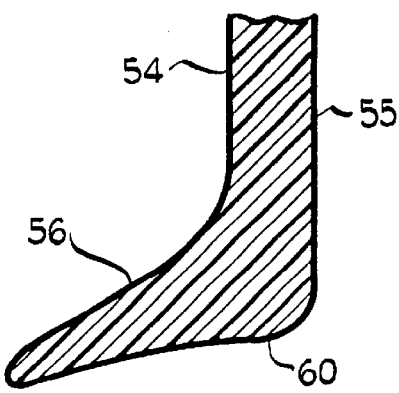
FIG. 6f of the drawings is a partial cross-sectional view showing in particular a seventh embodiment of the barrier.

In embodiments that employ a first vacuum seal means, the pressing of the seal member against the eye forces material from within the cavity either through a valve on the seal member (wherein the device is equipped with same) or beyond the barrier (wherein the barrier is configured to permit such egress, for example, the barrier of FIG. 6f). Once the user releases the pressure placed upon the seal member, the seal member returns toward its original configuration, and, in turnachieves a vacuum/suction effect between cavity 57 and the surface of the eye.

As shown in FIG. 7, after placement, the apparatus is generally partially covered by an eyelid of the patient such that a majority of the apparatus is not visible and so that the eyelid can provide an additional force to bias the apparatus against the surface of the eye so that the barrier can remain firmly against the surface of the eye. Furthermore, since the cornea region of the eye remains undisturbed, the patient's vision generally remains substantially unobstructed. Once fully positioned, the electrode is energized and the medicament is delivered iontophoretically. Due to the effective seal of barrier 60 relative to the surface of the eye, tears and other fluid (which can dilute or alter the condition of the medicament) are substantially precluded from entry into reservoir 12. Similarly, the medicament is precluded from flowing beyond the barrier and along the surface of the eye.

Once the treatment is complete, the apparatus is de-energized and removed from the eye. In particular, as the medical professional removes the apparatus, barrier 60 disengages from the surface of the eye. Due to the configuration of the barrier member and the type of material utilized, disengagement thereof from the surface of the eye can be achieved without adversely affecting the surface of the eye (even where the embodiment includes vacuum/suction forming means 71).

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. An ocular iontophoretic apparatus comprising:

a reservoir having an outer rim, the outer rim including a barrier;

the barrier being positionable upon the surface of the eye, thereby providing seal between the reservoir and the surface of the eye, to, in turn, substantially preclude the passage of fluid therebetween, wherein the barrier includes means for forming a vacuum/suction seal with a surface of the eye and a contact region having a concave configuration; and an electrode associated with the reservoir to provide iontophoretic current to the reservoir.

2. The ocular iontophoretic apparatus of claim 1 wherein the barrier comprises:

a first lobe and a second lobe, the first and second lobes extending away from each other at a predetermined angle.

3. The ocular iontophoretic apparatus of claim 1 wherein a portion of the barrier comprises a material having a Shore A hardness ranging between 5 and 60, and preferably between 5 and 25, to, in turn, preclude the passage of fluid into and out of the barrier.

4. The ocular iontophoretic apparatus of claim 1 wherein the barrier includes a first region and a second region, the second region comprising a material having a greater hardness than that of the first region.

5. The ocular iontophoretic apparatus of claim 4 wherein the second region comprises a Shore A hardness ranging between 5and 60.

6. The ocular iontophoretic apparatus of claim 4 wherein the outer rim is configured so as to follow the contours of a particular region of the sclera of an eye, to in turn, facilitate the uniform contact of the barrier against the surface thereof.

7. The ocular iontophoretic apparatus of claim 6 wherein the outer rim includes at least a double arcuate configuration, to, in turn, facilitate the uniform contact of the barrier against the surface of an eye.

8. The ocular iontophoretic apparatus of claim 7 wherein the first arcuate configuration includes a radius of curvature which ranges between 10 and 14 mm.

9. The ocular iontophoretic apparatus of claim 7 wherein the second arcuate configuration includes a radius of curvature which ranges between 10 and 14 mm.

10. The ocular iontophoretic apparatus of claim 1 further comprising means for vacuum sealing the reservoir against the surface of an eye of a patient.

11. The ocular iontophoretic apparatus of claim 10 wherein the vacuum sealing means comprises the cooperation of the barrier member and the seal member to facilitate the egress of a quantity of material from within the reservoir, while substantially precluding the ingress of material into the reservoir.

12. The ocular iontophoretic apparatus of claim 10 wherein the vacuum sealing means further includes a valve capable of selectively placing the reservoir in fluid communication with ambient surrounding conditions.

* * * * *